United States Patent [19]

Ueda

[11] Patent Number: 5,093,001

[45] Date of Patent: Mar. 3, 1992

[54] METHOD FOR RECOVERING CRYSTALS FROM SLURRY

[75] Inventor: Masanori Ueda, Kuga, Japan

[73] Assignee: Mitsui Petrochemical Industries, Ltd., Tokyo, Japan

[21] Appl. No.: 457,773

[22] PCT Filed: May 29, 1989

[86] PCT No.: PCT/JP89/00529

§ 371 Date: Jan. 18, 1990

§ 102(e) Date: Jan. 18, 1990

[87] PCT Pub. No.: WO89/11323

PCT Pub. Date: Nov. 30, 1989

[30] Foreign Application Priority Data

May 27, 1988 [JP] Japan .................. 63-129540

[51] Int. Cl.$^5$ .............................................. B01D 33/06
[52] U.S. Cl. .................................... 210/403; 210/404
[58] Field of Search ........ 210/784, 783, 791, 402-404, 210/161, 174, 210-215, 217; 162/357, 323-335

[56] References Cited

U.S. PATENT DOCUMENTS 4,263,148 4/1981 Symens et al. ................... 210/727

FOREIGN PATENT DOCUMENTS 705139 4/1941 Fed. Rep. of Germany .
1165430 3/1941 U.S.S.R. .
60537 3/1961 U.S.S.R. .

Primary Examiner—Frank Sever
Attorney, Agent, or Firm—Sherman and Shalloway

[57] ABSTRACT

A method for recovering crystals from a slurry by supplying the slurry to a rotary sucking filter while rotating a cylindrical filter medium thereof to effect a sequence of operations of sucking filtration, washing and further sucking filtration, which method comprises conducting a sucking filtration while pressurizing the slurry side so as to maintain such a temperature and pressure that the filtrate of the rotary sucking filter will not reach a condition of supersaturation, whereby stuffing of the filter medium due to deposition of crystals from the mother liquor with increase in the slurry viscosity is prevented and the recovery of the crystals are realized efficiently over a long period of time. This method is suitable for recovering crude and purified crystals of terephthalic acid and can be applied also for the recovery of general crystilline products, such as hydroquinone, resorcin and so on from slurries of them.

4 Claims, 2 Drawing Sheets

METHOD FOR RECOVERING CRYSTALS FROM SLURRY

TECHNICAL FIELD OF THE INVENTION

The present invention relates to a method for recovering crystals from a slurry containing crystals of, for example terephthalic acid.

BACKGROUND ART

In the production of terephthalic acid by a liquid phase oxidation of paradialkylbenzene, terephthalic acid produced will deposit within the mother liquor as crystals forming a slurry containing crystals of terephthalic acid. By separating the crystals out of this slurry, a crude product of terephthalic acid is obtained. After dissolution of the resulting crude crystals and subjecting to purification by treatments by oxidation, reduction and so on, terephthalic acid is caused to deposit as crystals to form a slurry containing the crystals. By separating the crystals from this slurry, purified terephthalic acid is obtained.

In either of the above-mentioned cases, the slurry has heretofore been subjected to procedures of separating the crystals by filtration or by centrifugation, washing the so separated crystals by re-slurrying in a wash liquor, separating again the crystals from this re-slurry and, if necessary, repeating these operations. Such a conventional technique reveals disadvantages that the procedures are complicated and that a larger apparatus has to be installed therefor.

As an alternative for this technique, a method had been proposed in which a sucking filtration, filter cake washing and a further sucking filtration are successively effected within a rotary sucking filter (designated hereinafter as RSF. In this technique, a sequence of operations of a sucking filtration, a filter cake washing, a further sucking filtration and removal of the filtered cake is realized in succession while rotating a cylindrical filter medium (filter cloth), wherein an ordinary pressure prevails outside the filter medium and the filtration pressure is attained by sucking out of the internal of the filter medium. However, this technique has a disadvantage that the stuffing or blockage of the filter medium proceeds quite steeply and the operation of apparatus is forced to be interrupted.

The object of the present invention is to obviate the disadvantage mentioned above and to propose a novel method for recovering crystals from a slurry under the use of RSF, which enables to recover the crystals by effecting a sequence of operations of filtration, washing and further filtration without suffering from stuffing of the filter medium.

DISCLOSURE OF THE INVENTION

The present invention proposes a method for recovering crystals from a slurry by supplying the slurry to a rotary sucking filter while rotating a cylindrical filter medium thereof to effect a sequence of operations of sucking filtration, washing and further sucking filtration, said method comprising conducting a sucking filtration while pressurizing the slurry side so as to maintain such a temperature and pressure that the filtrate of the rotary sucking filter will not reach a condition of supersaturation.

Investigating the cause for the stuffing of filter medium upon recovery of crystals using an RSF, it has now been discovered that this is due to deposition, together with an increase in the viscosity of the slurry, of the solute from the mother liquor onto the surfaces of the filter medium resulting from supersaturation of the mother liquor reached by a decrease in the temperature of the slurry caused by the sucking of the filter drum. Therefore, the present invention incorporates a sucking filtration under a pressurized condition, in order to avoid the supersaturation of the mother liquor as mentioned above.

Thus, according to the present invention, the sucking filtration in the RSF is carried out while pressurizing the slurry side on the rotating filter medium so as to maintain such a temperature and pressure that the filtrate of the rotary sucking filter will not reach a condition of supersaturation. In this manner, a premature stuffing of the filter medium due to the deposition of crystals from the mother liquor together with an increase in the viscosity of the slurry is eliminated and the crystals can be recovered from the slurry at higher efficiency over a considerable long period of time.

THE BEST MODE OF REALIZATION OF THE INVENTION

Figure 1:
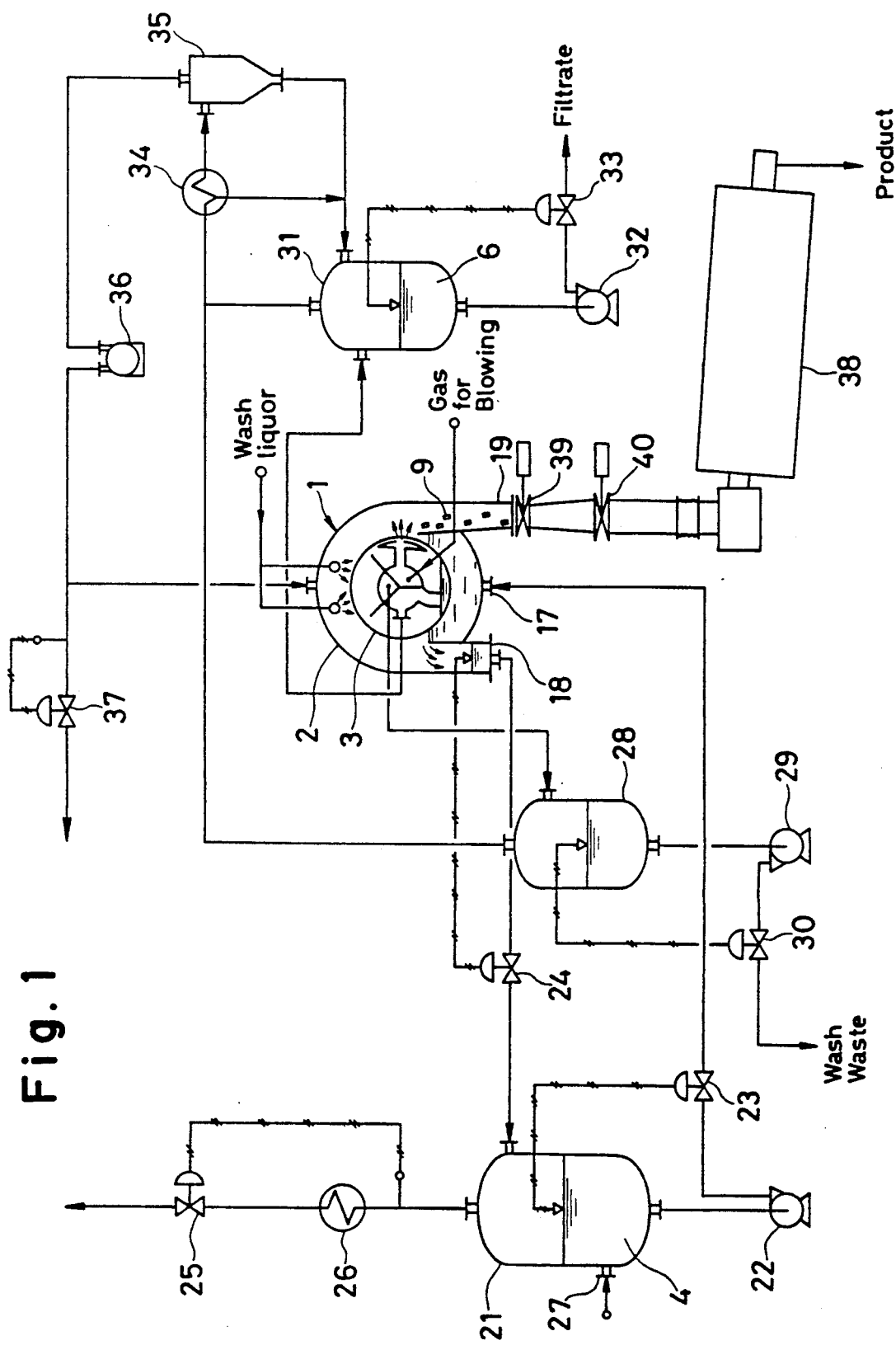
FIG. 1 shows a flow sheet of one embodiment of the method according to the present invention.
Figure 2:
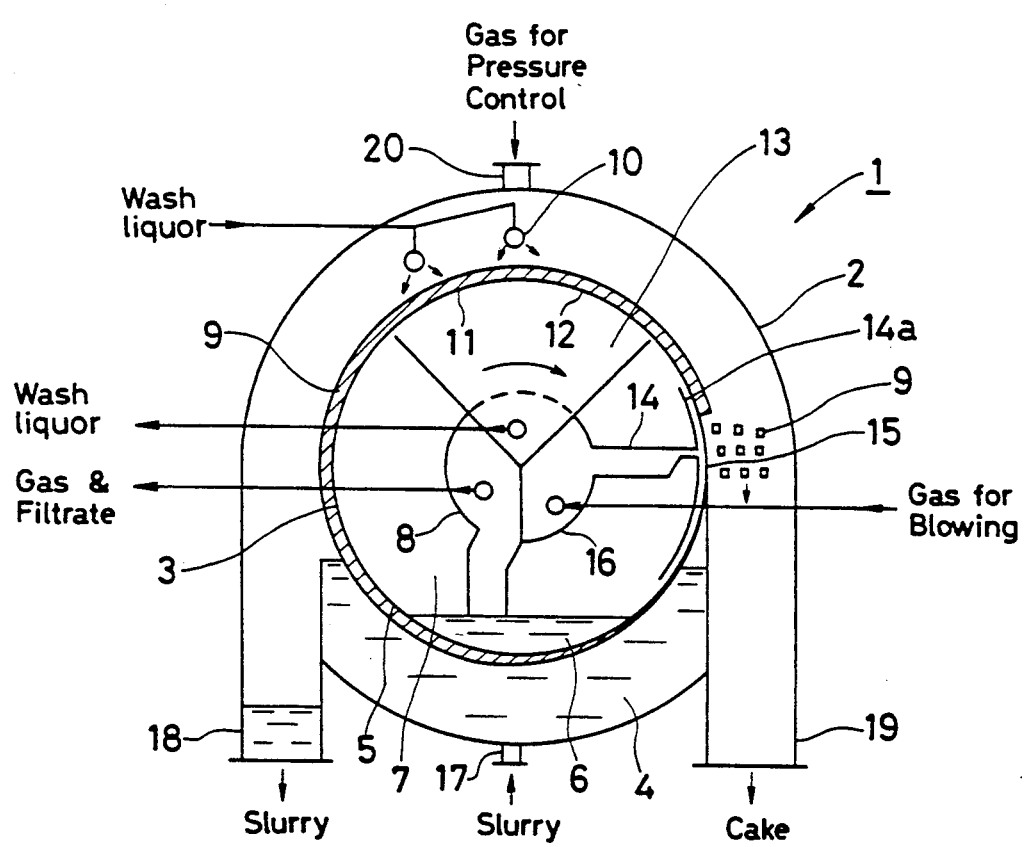
FIG. 2 is a schematic sectional view of the rotary sucking filter.

Below, the method according to the present invention will be described concretely with reference to the Drawings appended.

In the FIGS. appended, numeral 1 indicates an RSF housed by a casing 2 in which a horizontal cylindrical filter medium 3 is disposed in freely rotatable manner. The lower part of the filter medium 3 is soaked in a sump of slurry 4 formed inside the lower part of the casing 2 to form a filtering region 5, inside which there is provided an exhaustion unit 8 for sucking out internal gas 7 and the accumulated filtrate 6. Opposed to the upper portion of the filter medium, there is provided a spray unit 10 for spraying the wash liquor onto the filtered cake 9. Corresponding thereto, the filter medium 3 has a washing region 11 and, subsequent thereto, a de-liquoring region 12, inside which there is provided a collecting section 13 where the wash liquor is collected. In the further front and inside of the filter medium 3 are provided a blowing horn 14 and a gas seal 14a to be served for the removal of filtered cake 9 and the corresponding portion of the filter medium is constituted as cake removal zone 15, inside which is arranged a gas supply part 16 for supplying a blowing gas, such as nitrogen or so on. 17 denotes a slurry supply inlet, 18 a slurry accumulater, 19 a cake accumulator and 20 a gas inlet for regulating the pressure.

21 is a slurry reservoir from which the slurry is supplied to the RSF 1 at the slurry supply inlet 17 by a pump 22, while recirculating the slurry via the slurry accumulator 18. 23 is a control valve for keeping the liquid level in the slurry reservoir 21 constant and 24 is a control valve for maintaining the liquid level in the slurry accumulator 18 fixedly. 25 is a control exhaustion valve for exhausting the gas so as to maintain the internal pressure in the slurry reservoir 21. 26 is a condenser. 27 is a slurry make-up inlet.

28 is a wash waste tank in which the spent wash liquor collected in the collecting section 13 is accumulated and from which it is exhausted out of the system by a pump 29. 30 is a control valve operative so as to keep the liquid level in the wash waste tank 28 constant. 31 is a filtrate storage receiving the filtrate 6 and the gas 7 sucked out from the exhaustion unit 8 and exhausting the filtrate 6 by a pump 32. 33 is a level control valve operative for maintaining a constant liquid level in the filtrate storage 31.

The gas in the wash waste tank 28 and in the filtrate storage 31 is passed to a condenser 34 to effect condensation, the drain of which is separated by a drain separator 35 and the liquid phase separated is turned back to the filtrate storage 31, whereupon the gas is compressed by a compressor 36 and is then supplied to the gas inlet 20 as the pressure control gas. 37 is a pressure control valve operative so as to maintain a constant pressure of the pressure control gas. 38 is a drier which serves for drying the cake 9 discharged from the cake accumulator 19 via two closure valve means 39 and 40, from which it is taken out as refined crystals (product of manufacture).

For effecting the method for recovering the crystals, the slurry 4 stored in the slurry reservoir 21 is supplied to the sump of RSF 1 by a pump 22 and the filter medium 3 is caused to rotate so as to effect, in succession, the steps of sucking filtration, washing, sucking deliquoring and removal of the washed cake. Here, the compressed gas for controlling the filtration pressure is supplied via the gas inlet 20 to pressurize the slurry side 4, in order to maintain the filtrate 6 at such a pressure and temperature that no supersaturation thereof occurs, while sucking out the filtrate 6 and the gas 7 from the exhaustion unit 8 to effect sucking filtration in the filtering region 5. Here, the pressure on the side of the slurry corresponds to the sum of the filtering pressure drop and the pressure on the side of the filtrate. A sucking filtration is realized thereby, wherein the crystals suspending in the slurry 4 are retained on the rotating filter medium 3 and forms a layer of filtered cake 9 guided upwards, while a part of the slurry 4 is recirculated from the slurry accumulator 18 to the slurry reservoir 21.

Filtered cake 9 is washed in the washing region 11 by a wash liquor sprayed from the spray unit 10 and passes then to the de-liquoring region 12, where the wash liquor is removed, and turns downwards. In the cake removal zone 15, a blowing gas is supplied to the gas supply part 16 and is caused to blow out from the blowing horn 14 to remove the cake 9.

The filtrate 6 and the gas 7 sucked out of the exhaustion unit 8 are introduced into the filtrate storage 31, from which the filtrate 6 is exhausted by the pump 32.

The spent wash liquor exhausted from the collecting section 13 is introduced into the wash waste tank 28, from which it is discharged out of the system by the pump 29.

The gas accumulating in the wash waste tank 28 and in the filtrate storage 31 is passed via the condenser 34 to the drain separator 35, whereupon the gas separated from the condensed drain is compressed by the compressor 36 and the thus compressed gas is served for the filtration pressure control gas and is supplied to the gas inlet 20 to pressurize the side of the slurry 4 of the RSF 1.

By maintaining the filtrate 6 at such a pressure and temperature that no supersaturation thereof occurs upon sucking from the exhaustion unit 8 by pressurizing the slurry side of the RSF 1 by a pressure control gas, there occurs no supersaturation either in the slurry 4 and in the filtrate 6, so that no deposition of crystals nor increase in the viscosity of the slurry occurs and, thus, the problem of stuffing of the filter medium 3 is solved.

It is essential to adjust the internal pressure so as to avoid any deposition of the solute of the same material with the crystals to be recovered as well as of any impurity in the mother liquor. While the internal pressure on the side of the filtrate may occasionally reach a superatmospheric pressure, the filtration is effected even in such a case by the pressure difference between the slurry side and the filtrate side.

If the deposition of crystals is considerable due to the decrease in the temperature of the slurry by the heat dissipation from RSF 1, it is preferable to insulate the system and, if necessary, to maintain the temperature by installing a heat exchanger or the like.

The cake 9 removed in the cake removal zone 15 is taken out through the two closure valves 39 and 40 and is dried in the drier 38, before it is recovered therefrom as purified crystals (product of manufacture).

In the following, description is directed to Examples of the present invention.

EXAMPLE 1

A slurry of terephthalic acid/acetic acid (with 40% by weight of terephthalic acid, at 120° C.) resulting from an industrial production of terephthalic acid was treated by the method illustrated in the appended Figures to recover crude terephthalic acid crystals. Here, the slurry side in the RSF was maintained at a pressure of 1.5 Kg/cm$^2$ gauge at 120° C. and the filtrate side at a pressure of 1 Kg/cm$^2$ gauge at 120° C. The operation duration of the RSF until occurrence of stuffing of the filter medium was found to be 50 hours.

COMPARISON EXAMPLE 1

The procedures of Example 1 were repeated under a modification of the condition that the slurry side in the RSF 1 was maintained at the atmospheric pressure and at a temperature of 120° C. and the filtrate side was held at a pressure −400 mmHg lower than the atmospheric pressure and at a temperature of 100° C. The operation duration of the RSF until occurrence of stuffing of the filter medium was found to be only 1-5 minutes.

EXAMPLE 2

A slurry (with 50% by weight of terephthalic acid, 100° C.) resulting from re-slurrying the crystals obtained by subjecting the slurry as employed in Example 1 to a single centrifugation in accordance with the conventional practice was treated in the similar manner as described in Example 1. By maintaining the slurry side in the RSF at a pressure of 1.0 Kg/cm$^2$ gauge and a temperature of 110° C. and the filtrate side at a pressure of 0.5 Kg/cm$^2$ gauge and a temperature of 110° C., the operation duration of the RSF until occurrence of stuffing of the filter medium was found to be 100 hours.

COMPARISON EXAMPLE 2

The procedures of Example 2 were modified so that the slurry side in the RSF was maintained at the atmospheric pressure and a temperature of 110° C. and the filtrate side was held at a pressure −400 mmHg lower than the atmospheric pressure and at a temperature of 90° C. An operation duration until occurrence of stuffing of the filter medium was found to be 5 hours.

EXAMPLE 3

A terephthalic acid/water slurry (terephthalic acid concentration of 40% by weight, 150° C.) obtained by purifying the crude terephthalic acid product recovered in Example 1 by an oxidation-reduction treatment was treated in a similar manner as in Example 1 to recover the refined terephthalic acid crystals. By maintaining the slurry side in the RSF at a pressure of 5.5 Kg/cm$^2$ gauge and at a temperature of 150° C. and the filtrate side at a pressure of 5.0 Kg/cm$^2$ gauge at a temperature of 150° C., an operation duration until occurrence of stuffing of the filter medium was found to be 250 hours.

COMPARISON EXAMPLE 3

The procedures of Example 3 were modified, so that the slurry side in the RSF was maintained at atmospheric pressure at 100° C. and the filtrate side was maintained at a pressure $-400$ mmHg lower than the atmospheric pressure at 80° C. The operation duration of the RSF until stuffing of the filter medium was found to be 50 minutes.

APPLICABILITIES OF THE INVENTION IN INDUSTRY

The method according to the present invention is suitable for recovering crude and purified terephthalic acid crystalline products as explained above. It is applicable also for recovering other crystalline products in general from slurries containing them, such as, those in the production of hydroquinone, resorcin and so on.

I claim:

1. In a method for recovering crystals from a slurry by supplying the slurry to a rotary sucking filter while rotating a cylindrical filter medium thereof to effect a sequence of operations of sucking filtration, washing and deliquoring, the improvement comprising inhibiting blockage of the filter medium due to deposition of crystals from the mother liquor of the slurry and increase in viscosity of the slurry by conducting a sucking filtration while pressurizing the slurry side so as to maintain such a temperature and pressure that the filtrate of the rotary sucking filter will not reach a condition of supersaturation, and recovering the crystals whereby recovery of the crystals from the slurry can be effected at higher efficiency over long periods of time.

2. In a method for recovering crystals from a crystal-containing slurry which is capable of forming new crystals from the mother liquor upon temperature decrease, by the steps of filtering the slurry in a rotary sucking filter while supplying the slurry on a rotating cylindrical filter medium thereof to effect in sequence, the operations of sucking filtration, washing and deliquoring, the improvement comprising inhibiting blockage of the filter medium during filtration due to deposition of crystals from the mother liquor and increase in viscosity of the slurry, by conducting sucking filtration under pressurization of the slurry side of the filter medium while sucking out the filtrate from the filtrate side thereof, thereby establishing a pressure drop between the slurry side and the filtrate side necessary for effecting the filtration, and maintaining the rotary sucking filter under temperature and pressure which inhibits occurrence of supersaturation of the mother liquor and the filtrate.

3. In a process for recovering crystals from a crystal-containing slurry capable of forming new crystals from the mother liquor upon temperature decrease, by the steps of filtering the slurry in a rotary sucking filter while supplying the slurry on a rotating cylindrical filter medium thereof to effect in sequence, the operations of sucking filtration, washing and deliquoring, the improvement comprising inhibiting blockage of the filter medium during filtration by carrying out the sucking filtration under pressurization of the slurry side of the filter medium by supplying a pressure adjusting gas thereto while sucking out the filtrate from the filtrate side thereof, so as to establish a pressure drop between the slurry side and the filtrate side necessary for effecting the filtration and to maintain the mother liquor and the filtrate at a temperature and pressure which inhibits supersaturation of the solute; washing the filter cake retained on the rotating filter medium in the washing region; deliquoring the washed cake on the rotating filter medium by filtration in the deliquoring region; and removing the deliquored cake of crystals from the filter drum to recover it.

4. A process for recovering terephthalic acid as crystals from a crude terephthalic acid product slurry by filtering the slurry in a rotary sucking filter while supplying the slurry on a rotating cylindrical filter medium thereof to effect in sequence, the operations of sucking filtration, washing and deliquoring, said process comprising inhibiting blockage of the filter medium and recovering purified terephthalic acid crystals by conducting a sucking filtration while pressurizing the slurry side of the filter medium at 100°–160° C. and a pressure of 0.5–7 Kg/cm$^2$ gauge by supplying a pressure adjusting gas thereto while sucking out the filtrate from the filtrate side thereof, so as to establish a pressure drop between the slurry side and the filtrate side of 0.2–3 Kg/cm$^2$ gauge and to maintain the rotary sucking filter under a condition of temperature and pressure whereby supersaturation of the mother liquor and the filtrate is prevented and blockage of the filter medium is inhibited; washing the filtered cake retained on the rotating filter medium in the washing region; deliquoring the washed cake in the deliquoring region by filtration; and removing the deliquored cake of crystals from the filter drum to recover it, whereby high efficiency recovery of purified terephthalic acid crystals can be carried out for extended periods of time.

* * * * *

UNITED STATES PATENT AND TRADEMARK OFFICE
CERTIFICATE OF CORRECTION

PATENT NO. : 5,093,001

DATED : March 3, 1992

INVENTOR(S) : UEDA

It is certified that error appears in the above-identified patent and that said Letters Patent is hereby corrected as shown below:

Title page, change "[22] PCT Filed: May 29, 1989" to --[22] PCT Filed: May 26, 1989--

Column 6, line 28, change "filler" to --filter--.

Signed and Sealed this

Tenth Day of August, 1993

Attest:

MICHAEL K. KIRK

*Attesting Officer*     *Acting Commissioner of Patents and Trademarks*